US006303112B1

(12) United States Patent
Worden

(10) Patent No.: US 6,303,112 B1
(45) Date of Patent: Oct. 16, 2001

(54) ENRICHED PLATELET WOUND HEALANT

(76) Inventor: Charles E. Worden, 7201 Highway 300, Little Rock, AR (US) 72223

( * ) Notice: Subject to any disclaimer, the term of this patent is extended or adjusted under 35 U.S.C. 154(b) by 0 days.

(21) Appl. No.: 09/424,523

(22) Filed: Nov. 23, 1999

Related U.S. Application Data

(63) Continuation-in-part of application No. PCT/US99/02981, filed on Feb. 13, 1999.
(60) Provisional application No. 60/097,897, filed on Aug. 26, 1998, and provisional application No. 60/090,167, filed on Jun. 22, 1998.

(51) Int. Cl.⁷ .......................... A61K 31/74; A61K 9/127; A61K 31/045; A61K 31/04

(52) U.S. Cl. ................... 424/78.06; 424/450; 424/93.72; 514/724; 514/725; 514/946; 514/947

(58) Field of Search ................................ 424/450, 78.06, 424/93.72, 44; 514/724, 725, 946, 947

(56) References Cited

U.S. PATENT DOCUMENTS

| | | |
|---|---|---|
| 3,628,974 | 12/1971 | Battista et al. . |
| 3,883,574 | 5/1975 | Axen . |
| 3,948,875 | 4/1976 | Cohen et al. . |
| 4,177,261 | 12/1979 | Dietze et al. . |
| 4,251,510 | 2/1981 | Tankersley . |
| 4,272,521 | 6/1981 | Zuffi . |
| 4,272,523 | 6/1981 | Kotitschke et al. . |
| 4,273,871 | 6/1981 | Tolbert et al. . |
| 4,287,180 | 9/1981 | Thomas . |
| 4,287,184 | 9/1981 | Young . |
| 4,294,826 | 10/1981 | Feldman . |
| 4,296,100 | 10/1981 | Franco . |
| 4,298,598 | 11/1981 | Schwarz et al. . |
| 4,350,687 | 9/1982 | Lipton et al. . |
| 4,378,347 | 3/1983 | Franco . |
| 4,427,650 | 1/1984 | Stroetmann . |
| 4,427,651 | 1/1984 | Stroetmann . |
| 4,431,582 | 2/1984 | Stenn . |
| 4,444,760 | 4/1984 | Thomas, Jr. . |
| 4,465,669 | 8/1984 | Wissler et al. . |
| 4,470,968 | 9/1984 | Mitra et al. . |
| 4,470,969 | 9/1984 | Pancham et al. . |
| 4,471,053 | 9/1984 | Comi et al. . |
| 4,472,523 | 9/1984 | Welcj et al. . |
| 4,479,896 | 10/1984 | Antoniades . |
| 4,479,938 | 10/1984 | Thomas . |
| 4,503,038 | 3/1985 | Banda et al. . |
| 4,512,977 | 4/1985 | Lundy . |
| 4,514,387 | 4/1985 | Wissler . |
| 4,529,590 | 7/1985 | LeVeen et al. . |
| 4,621,052 | 11/1986 | Sugimoto . |
| 4,727,137 | 2/1988 | Vallee et al. . |
| 4,919,939 | 4/1990 | Baker . |
| 5,073,114 | 12/1991 | Detsch . |
| 5,077,049 | 12/1991 | Dunn et al. . |
| 5,115,096 | 5/1992 | Shoyab et al. . |
| 5,149,691 | 9/1992 | Rutherford . |
| 5,155,038 | 10/1992 | Eyal et al. . |
| 5,158,934 | 10/1992 | Ammann et al. . |
| 5,165,938 | 11/1992 | Knighton . |
| 5,278,201 | 1/1994 | Dunn et al. . |
| 5,294,446 | 3/1994 | Schlameus et al. . |
| 5,366,733 | 11/1994 | Brizzolara et al. . |
| 5,368,859 | 11/1994 | Dunn et al. . |
| 5,376,636 | 12/1994 | Rutherford et al. . |
| 5,405,607 | 4/1995 | Epstein . |
| 5,422,340 | 6/1995 | Ammann et al. . |
| 5,580,923 | 12/1996 | Yeung et al. . |
| 5,585,007 | 12/1996 | Antanavich . |
| 5,589,462 | 12/1996 | Patat et al. . |
| 5,599,558 | 2/1997 | Gordinier et al. . |
| 5,604,204 | 2/1997 | Ammann et al. . |
| 5,607,694 | * 3/1997 | Marx ................................... 424/450 |
| 5,648,265 | 7/1997 | Epstein . |
| 5,648,380 | 7/1997 | Martin . |

(List continued on next page.)

FOREIGN PATENT DOCUMENTS

| | | |
|---|---|---|
| 0 105 014 A2 | 4/1984 | (EP) . |
| 0 128 849 A1 | 12/1984 | (EP) . |
| 0 190 018 A2 | 3/1986 | (EP) . |
| 2 472 385 | 7/1981 | (FR) . |
| 2 533 438 A2 | 3/1984 | (FR) . |
| 2 146 335 A | 4/1985 | (GB) . |
| WO 87/01728 | 3/1987 | (WO) . |
| WO 98/32675 | 7/1998 | (WO) . |
| WO 99/20288 | 4/1999 | (WO) . |

OTHER PUBLICATIONS

J. Murphy, "Block a Protein, Starve a Tumor: Scientist reproduce a growth signal for capillaries," *Time Magazine*, from Oct. 7, 1985 pp. 62.

"Hemostasis and Blood Coagulation," Blood Cells, Immunity, and Blood Clotting, pp. 99–110 (1995).

Cope, Lewis, "Surgeon's treatment lets patients heal stubborn wounds with own blood," *Minneapolis Star and Tribune*, Nov. 12, 1984.

Antoniades et al., "Radioimmunosassy of a human serum growth factor for Balb/c–3T3 cells: Derivation from platelets," *Proc. Natl. Acad. Sci.*, vol. 74, pp. 1973–1977 (1997).

Carpenter, "The Regulation of Cell Proliferation: Advances in the Biology and Mechanism of Action of Epidermal Growth Factor" *J. Invest Dermatol.*, vol. 71, pp. 283–288 (1978).

Deuel et al., "Platelet factor 4 is Chemotactic for Neutrophils and Monocytes," *Proc. Natl. Acad. Sci.*, vol. 78, pp. 4584–4587 (1981).

(List continued on next page.)

*Primary Examiner*—Zohreh Fay
*Assistant Examiner*—Brian-Yong S. Kwon
(74) *Attorney, Agent, or Firm*—Joe D. Calhoun

(57) ABSTRACT

A wound healant composition comprising a therapeutically effective amount of activated growth factors and ascorbic acid and/or at least one retinoid and/or at least one antibiotic, that facilitates the growth of new tissue.

24 Claims, No Drawings

U.S. PATENT DOCUMENTS

| | | |
|---|---|---|
| 5,656,587 | 8/1997 | Sporn et al. . |
| 5,658,592 | 8/1997 | Tanihara et al. . |
| 5,658,956 | 8/1997 | Martin et al. . |
| 5,658,957 | 8/1997 | Martin . |
| 5,661,127 | 8/1997 | Bhatnagar et al. . |
| 5,674,912 | 10/1997 | Martin . |
| 5,686,116 | 11/1997 | Bockman et al. . |
| 5,692,302 | 12/1997 | Martin et al. . |
| 5,705,477 | 1/1998 | Sporn et al. . |
| 5,714,159 | 2/1998 | Shalaby . |
| 5,733,545 * | 3/1998 | Hood .................................. 424/93.72 |
| 5,733,884 | 3/1998 | Barbul et al. . |
| 5,811,094 | 9/1998 | Caplan et al. . |
| 5,852,004 | 12/1998 | Barritault et al. . |
| 5,854,207 | 12/1998 | Lee et al. . |
| 5,856,364 | 1/1999 | Martin . |
| 5,863,938 | 1/1999 | Martin . |
| 5,874,109 | 2/1999 | Ducheyne et al. . |
| 5,874,479 | 2/1999 | Martin . |
| 5,885,829 | 3/1999 | Mooney et al. . |
| 5,891,558 | 4/1999 | Bell et al. . |
| 5,899,939 | 5/1999 | Boyce et al. . |
| 5,900,245 | 5/1999 | Sawhney et al. . |
| 5,904,718 | 5/1999 | Jefferies . |
| 5,910,492 | 6/1999 | Hoshino et al. . |
| 5,916,870 | 6/1999 | Lee et al. . |
| 5,948,428 | 9/1999 | Lee et al. . |
| 5,952,010 | 9/1999 | Constantz . |
| 5,981,606 * | 11/1999 | Martin .................................. 514/724 |
| 6,001,352 | 12/1999 | Boyan et al. . |
| 6,005,162 | 12/1999 | Constantz . |
| 6,015,474 | 1/2000 | Stedronsky . |
| 6,051,248 | 4/2000 | Sawhney et al. . |
| 6,051,648 | 4/2000 | Bhee et al. . |
| 6,054,122 | 4/2000 | MacPhee et al. . |
| 6,056,715 | 5/2000 | Demopulos et al. . |
| 6,056,970 | 5/2000 | Greenawalt et al. . |
| 6,071,284 | 6/2000 | Fox . |
| 6,083,523 | 7/2000 | Dionne et al. . |
| 6,083,902 | 7/2000 | Cederhom-Williams . |
| 6,086,863 * | 7/2000 | Ritter et al. ...................... 424/78.06 |

OTHER PUBLICATIONS

"Evaluation of the efficacy and safety of Platelet Derived Wound Healing Formula (PDWHF, Homologous) in the treatment of chronic, nonhealing, cutaneous wounds: A multicenter, radomized, double–blind, placebo–controlled study: Protocol 202," Prepared by CuraTech, Inc., Dec. 20, 1988.

"executive Summary: Platelet Derived Wound Healing Formula (PDWHF), Wound Care Center Program," Prepared by Curatech, Inc.

Frati et al., "Selective Binding of the Epidermal Growth Factor and Its Specific Effects on the Epithelial Cells of the Cornea," *Exper. Eye Res.*, vol. 14, pp. 135–141 (1972).

Greaves, "Lack of Effect of Topically Applied Epidermal Growth Factor (EGF) on Epidermal Growth in Man in vivo,"*Clinical and experimental Dermatology*, vol. 5, pp. 101–103 (1980).

Grotendorst "Can Collagen Metabolishm Be Controlled?"*J. Trauma.* vol. 24, pp. 49–54;, (1984).

Grotendorst, G.R et al., "Platelet–Derived Growth Factor is a Chemoattractant for Vascular Smooth Muscle Cells", *Journal of Cellular Physiology*, vol. 113, pp. 261–266 (1982).

Grotendorst, G.R. et al., "Molecular Mediators of Tissue Repair" *Surgical Science Series*, vol. 2, pp. 20–40 (1984).

Grotendorst, Gary R. et al., "Stimulation of Granulation Tissue formation by PDGF in Normal and Diabetic Rats," (25 pages), manuscript.

Höckel, Michael, et al., "Purified Monocyte–derived Angiogenic Substance (Angiotropin) Induces Controlled Angiogenesis Associated with Regulated Tissue Proliferation in Rabbit Skin," *J. Clin. Invest.* , vol. 82, pp. 1075–1090 (1988).

Hunt, T. "Can Repair Processes be Stimulated by Modulators (Cell Growth Factors, Angiogenic Factors, etc.) without Adversely effecting Normal Processes?" *Frontiers in Understanding Burn Injury*, 24(9) Supplement: S39–S46 (1984).

Johnsson, A., et al., "Platelet–Derived Growth Factor: Identification of Constituent Polypeptides Chains" *Biochemical and Biophysical Research Communications*, vol. 104, No. 1, pp. 67–74 (1982).

Knighton, D.R., et al., "Classification and Treatment of Chronic Nonhealing Wounds: Successful Treatment with Autologous Platelet–derived Wound Healing Factors (PDWHF)"*Annals of Surgery*, vol. 204 No. 3, pp. 322–330 (1986).

Knighton, D.R., et al., "Role of Platelets and Fribrin in the Healing Sequence," *Annals of Surgery*, vol. 196, No. 4, pp. 379–388 (1982).

Knighton, D.R., et al., "The Use of Platelet Derived Wound Healing Formula In Human Clinical Trials," pp. 1–12 (1987).

Leitzel et al., "Growth Factors and Wound Healing in the Hamster," *J. Dermetal. Surg. Oncl.*, vol. 11, No. 6, pp. 617–622 (1985).

Linman, James MD, "Hemorrhagic Disorders" *Hematology* pp. 849–894 (1975).

M.S. Banda et al., "Isolation of a nonmitogenic angiogenesis factor from wound fluid" *Proc. Nat'l Acad. Sci. US.S.A.*, pp. 773–777 (1982).

Michaeli, D., et al.,"The Role of Platelets in Wound Healing: Demonstration of Angiogenic Activity," *Soft and Hard Tissue Repair*, pp. 380–394.

Niall et al., "The Effect of Epidermal Growth Factor on Wound Healing in Mice" *J. Surg Res.*, vol. 33, 164–169 (1982).

Sederma, Brochure: "Repair Factor F.C.P." (41 Pages).

Robson., M.C., et al., "Platelet–derived growth factor BB for the Treatment of chronic pressure ulcers," *The Lancet.*, vol. 339, pp. 23–25 (1992).

Ross, R., and Vogel, A., "The Platelet–Derived Growth Factor,"(full citation not know) pp. 203–210 (1978).

Senior, et al., "Chemotactic Activity of Platelet Alpha Granule Proteins for Fibroblasts" *The Journal of Cell Biology*, vol. 96, pp. 382–385 (1983).

Sporn, M., et al., "Polypeptide Transforming Growth Factors Isolated from Bovine Sources and Used for Wound Healing in vivo,"*Science.*, vol. 219, 1329–1331 (1983).

Thorton et al., "Epidermal Growth Factor In the Healing of Second Degree Burns: a controlled Animal Study," *Burns*, vol. 8, 156–160 (1981).

Zetter, Bruce R. and Harry N. Antoniades, "Stimulation of Human Vascular Endothelial Cell Growth by a Platelet–Derived Growth Factor and Thrombin," *Journal of Supermolecular Structure*, pp. 361–370 (1979).

Clewell, K., "Topically applied ascorbic acid enhances wound healing and production of connective tissue protein," BIOSIS on STN, 1993:356018 (Abstract) 1993.

Macphee, et al., "Supplemental and unsupplemental tissue sealants, methods of their production and use," Database HCAPLUS as STN, 126:135685 (Abstract).

Mann, "Wound Healing Compositions," Database HCAPLUS as STN, 103:59296 (Abstract).

Saika, "Effect of L–ascorbic acid 2–phosphate on corneal wound heal," 115:225439 (Abstract) 1993.

* cited by examiner

ENRICHED PLATELET WOUND HEALANT

This application is a continuation-in-part application of pending utility patent application number PCT/US99/02981 filed Feb. 13, 1999 with the United States Patent Office as Receiving Office, which in turn claims a priority filing date based on United States provisional application No. 60/090,167 filed Jun. 22, 1998 and United States provisional application No. 60/097,897 filed Aug. 26, 1998.

BACKGROUND OF THE INVENTION

The invention disclosed herein generally relates to a composition of matter used in the treatment of wounds, a method of making same, and a method of using same.

There have been many different substances and methods developed in the past for treating wounds, depending upon the type and location and severity of the wound. A wound is generally defined as an injury to an area of the body of a human or animal. Although injury to the surface of the skin is the most well known type of wound, the surfaces of internal organs may also be wounded, such as during surgery, rupture of the spleen or liver, or resulting from traumatic blows to the body surface in the vicinity of an internal organ.

Medical practice characterizes wounds as chronic or acute, according to the persistency and severity of the wound. A chronic wound is one that is prolonged or lingering, rather than promptly healed. An acute wound is one that occurs relatively quickly, and heals relatively quickly as well. Tissue wounds may have a wide spectrum of manifestations, as small as merely an abnormal microscopic tear or fissure in tissue (or a surface thereof), or as large as the abrasion or ablation of the skin covering a substantial portion of the body, such as in a burn victim. Acute wounds covering a large or movable surface are usually the most difficult to guard from infection, and to heal.

The invention described herein is primarily related to substances topically applied to the exterior surface of chronic wounds, although the invention described herein also has some applications for facilitating the healing of other wounds such as acute wounds. The composition of matter described herein is especially suited to topical application to burn wounds and chronic lesions, such as ulcers on the feet of diabetics. However, the compositions of matter and the methods described herein are not limited solely to that topical application.

Wound healing is affected by the presence of various substances found in the blood and bodily fluids. The blood is the primary medium for delivering healing agents to the wound site, and for transporting foreign or harmful substances away from the wound. Whole blood is primarily comprised of three main types of cells suspended in a protein rich solution known as plasma.

The three main cell types of whole blood are erythrocytes (a.k.a. red blood cells), leukocytes (a.k.a. white blood cells) and thrombocytes (a.k.a. platelets). The red blood cells are the iron-containing cells that facilitate the transport and transfer of oxygen to body tissue, and the removal of carbon dioxide. The white blood cells perform functions such as phagocytosis of foreign bodies and production of antibodies, primarily responsible for fighting infection and foreign substances within the blood or wound site. Platelets perform many functions such as plugging leaks in blood vessels and helping begin the process leading to the formation of a blood clot; platelets contain substances known as growth factors that facilitate the formation of new tissue.

Although there are several methods for separating whole blood into its various components, one of the most convenient and expeditious methods is accomplished by differentially centrifuging blood or some of its components (i.e., apheresis). In this way, the red and white blood cells and plasma may be separated out and returned to the donor's or patient's body, leaving the sequestered platelets in essentially concentrated form for use in wound healing techniques. From blood extracted from a patient, the platelets may thus be obtained and activated for use on the same patient; methods of using a patient's own blood are called "autologous" or "autogenic" donor methods. Methods using blood donated by one or more third parties for use by a patient are called "homologous" or "heterologous" donor methods, or collectively called "allogenic" methods.

One of the proteins suspended in plasma is fibrinogen, which reacts with substances released into (or attracted by) wound sites to produce sticky strands offibrin. Such reactions result in the cross linking of the strands to form a mesh that holds and supports the deposit or growth of other tissue materials at the wound site.

The wound healing process is generally considered to occur in several stages, generally know as the healing cascade. After tissue injury, platelets are among the first cells to appear in the vicinity of the wound. Activation of a platelet by an agonist such as thrombin, or other agonists such as those listed elsewhere herein, leads to the release of granule material from within the platelet. Such granulation activation results in the release of proteins known as growth factors, primarily concentrated in the alpha granules of platelets. These released growth factors stimulate the formation of new tissue; when applied to wounds, growth factors have been known to increase the rate of collagen laydown, vascular ingrowth, fibroblast proliferation and overall healing. The release of a protein known as platelet-derived growth factor (PDGF) is a chemotactic for monocytes, neutrophils and fibroblasts into the wound, to begin the inflammatory stage of the healing process. During this time, monocytes secrete PDGF and another platelet protein known as transforming growth factor-$\beta1$, which recruits and activates fibroblagts, a prerursor to fibrinogen, to begin the repair stage of the healing process. Subsequently, wound healing continues through the process of collagen remodeling within the wound.

The presence of growth factors promotes wound healing. The invention described herein increases the amount of growth factors in the wound, and thereby facilitates the promotion of the healing rate. This may be especially important in "wounded" patients, especially those with chronic wounds who may lack sufficient circulation to facilitate the healing cascade. The invention described herein also facilitates the covering of the wound area with a substance that prevents or helps to reduce infection caused by most bacteria; and to the extent that the wound treatment material is made from autologous blood or similar biological materials, the invention described herein reduces the risks associated with the use of treatment materials made from biological materials obtained from one or more third parties. An autologous product avoids some of the common problems associated with the use of biological materials from third parties, such as (for example) screening to assure that the donor was biologically or immunologicaly compatible with the patient, and otherwise free of hepatitis, HIV and the like.

Base upon the foregoing general scientific principles, already known in the field are wound sealants made from biological materials obtained primarily from tissue other than blood platelets. For example, wound sealants include "fibrin glue," which often is essentially a mixture of co-coagulants (thrombin and calcium), concentrated fibrinogen and other coagulation proteins. In most applications, the primary roles of fibrin glue are to seal wound surfaces to prevent loss of blood and other body fluids after surgery, and to provide adhesion between adjacent tissue surfaces. These products form a hard, cast-like covering over the area to be sealed, and tend to be non-yielding to limb movement.

The production of fibrin glue often requires obtaining fibrinogen from blood through a process known as cryoprecipitation, including both freeze-thaw cycles and relatively lengthy centrifuigation of plasma in controlled environments, to concentrate the fibrinogen in large enough amounts required for use; the precipitant thus obtained is frozen to −20° to −30° centigrade before storage. These requirements make such materials unsuitable for application during the course of surgery, especially emergency surgery without an hour or more lead time; moreover, to the extent this process depends upon the use of autologous biological materials, using this process shortly before or during surgery may result in the loss of crucial bodily fluids during a time when the patient's body is badly in need of such fluids. By contrast, substantially larger amounts of concentrated platelets can be more conveniently obtained within a matter of minutes from more recent methods of differential blood centrifugation not requiring freezing, without significant loss of bodily fluids.

To date, there has been much research concerning fibrin glue. This is considered to be a separate field from the present invention, primarily because fibrin glues typically contain cryoprecipitated proteins without platelets. The use of fibrin glue is discussed extensively in the scientific literature; for example, see the references cited in U.S. Pat. No. 5,585,007 issued to Antanavich et al on Dec. 17, 1996.

One method of differential centrifuigation essentially allows separating the patient's own blood into at least three different components: packed erythrocytes (red blood cells), plasma and platelet concentrate. Platelet concentrate can be combined with a solution of either sodium or calcium mixed with thrombin ("calcified thrombin"), often to form a gelatinous composition of activated platelets that, when made with the necessary viscosity, can be utilized as a wound sealant. Such sealants typically set up into a hard mass covering the application site, thereby sealing the site. The initially sticky, gelatinous state usually hardens to serve the functions of (1) stopping the loss of blood and other bodily fluids, because it effectively acts as a patch; (2) sealing wounds against external contaminants; and (3) preventing traditional problems associated with the mere stitching of wounds.

Wound healing compositions including platelets have advantages over materials without platelets. One reason is that natural wound healing agents are released by the platelets. Further, the concentration of platelets likewise allows for a concentrated amount of wound healing factors. Additionally, to the extent that the wound healing composition is made from the biological materials of the patient, the risks associated with heterologous donors (such as disease, immunologic reactions, or the like) are eliminated.

The work surrounding the field of autologous platelet gel to date has focused on perioperative blood treatment (hemostatic effect)—preventing loss of blood during or immediately following surgery. Normally, when a patient is on the operating table, the patient will lose large amounts of blood and other bodily fluids, depending upon the type of surgery involved. To counter this blood loss, the traditional approach is to infuse the patient with blood, which is usually donated from one or more third parties (or sometimes donated by the patient in anticipation of surgical needs). There exists many different types of methods for collecting blood that are normally used in this type situation.

Because there is obviously an increased risk of disease, immunologic reaction, or other complications associated with procedures including heterologous blood donation, recent efforts have been made to use blood contemporaneously obtained from the patient during surgery. This blood can be fractionated and/or filtered, and subsequently re-infused into the patient, saving much time, expense, bodily fluids and avoiding normal risks discussed above.

It is from the perioperative blood treatment arena that the uses for autologous platelet gel were focused. The use of platelet gel on open wounds resulting from surgery have recently met great success. This particular use allows the patient to keep his/her own blood and also reduce costs.

The following patents are arguably related to the invention disclosed herein:

| Patent Number | Inventor | Date |
| --- | --- | --- |
| 5,733,545 | Hood | March 31, 1998 |
| 5,585,007 | Antanavich, et al. | December 17, 1996 |
| 5,165,938 | Knighton | November 24, 1992 |
| 5,674,912 | Martin | October 7, 1997 |

However, the inventions disclosed therein are patentably distinct from the invention disclosed herein.

The Hood patent claims a plasma-buffy coat concentrate comprising plasma, platelets (at a concentration of at least $10^9$ cells/ml), fibrinogen (at a concentration of at least 5 mg/ml), and white blood cells (at a concentration of at least 3 times $10^7$ cells/ml). The Hood invention achieves hemoconcentration by removal of water from plasma. The Hood invention also fails to recognize the benefits of increased levels of vitamins, antibiotics and other substances. For instance, higher amounts of vitamin C is believed to prolong the viscosity and longevity of a gelatinous composition of fibrinous matter derived substantially from platelets. As another example, the Hood invention fails to recognize the benefits of including retinoids, such as vitamin A (retinol) and/or vitamin E. For instance, patients undergoing treatment including steroids often have immune systems that are suppressed, or otherwise non-responsive to stimuli; increased amounts of vitamin A are known to counteract that non-responsiveness, and thereby facilitate the promotion of wound healing. Similarly, increasing the level of vitamin E is believed to facilitate the promotion of wound healing.

The Knighton patent discloses the use of isolated multiple growth factors combined with a biologically compatible carrier substance, after sequestration (and removal) of all platelet membranes and plasma containing fibrin from the growth factor exudate prepared. Discarding such membranes essentially removes from the composition residual growth factors known to be concentrated in the membranes, and potential receptor sites for facilitating matrix formation. The method utilized in Knighton also requires a number of time consuming and labor intensive steps, including storage at −20° to −30° centigrade prior to use. The Knighton method also requires that wound treatments be repeated on a daily basis.

The Antanavich patent discloses a composition based primarily on plasma and, like Knighton, requires a biologically acceptable carrier for administering a plasma concentrate comprising platelets, fibrinogen and fibrinectin. The Antanavich composition is essentially a fibrin glue meant to have a high tensile strength (viscosity), sufficient to seal a wound.

To the extent that the Martin patent is relevant, Martin discloses a composition comprising a sunscreen agent, an anti-inflammatory agent, and a wound healing composition. (Martin, column 6 line 66 through column 7 line 2.) Said wound healing composition comprises the combination of pyruvate, an anti-oxidant (including vitamins A, C and E), and fatty acids required for repairing cellular membranes. (Martin, column 7 lines 2 through 8.) The utility and function of said vitamins to the Martin composition, intended for use in sunlight rather than shielded from sunlight, are distinctly different from the utility and function of the vitamins to the invention disclosed herein, as explained hereinbelow.

The chemical reactions and cascades that normally happen when thrombin is added to the concentrated platelets are indeed complex. They are discussed in the scientific article by Reeder, et al, in *Proceedings of the American Academy of Cardiovascular Perfusion*, Vol. 14, January 1993. Adding a preservative, or healing promotion materials that do not detract from, substantially interfere with, or even destroy these different reactions is the crux of the invention disclosed herein.

One object of the invention is to provide a wound treatment material that is capable of quick and convenient production in the presence of the patient.

Another object of the invention is to provide a wound treatment material that facilitates the promotion of wound healing.

Another object is to provide a wound treatment material that facilitates the prevention of wound infection.

Another object is to provide a method of making a wound treatment material satisfying the objectives expressed, implied or inherent herein.

Another object is to provide a method of using a wound treatment material satisfying the objectives expressed, implied or inherent herein.

SUMMARY OF THE INVENTION

In most general terms, the invention described herein expands the uses for concentrated platelet materials, especially those in gel form, by improving the speed and convenience of making the composition; the invention described herein also improves the performance of the concentrated platelet composition, by making it more useable for applications over longer periods of time, and by enhancing the wound healing and infection fighting properties. For autologous platelet gel to be more useful, the gelatinous state must be capable of remaining stable for a reasonable period of time. One aspect of the present invention is to add a preservative to the platelet gel, such as ascorbic acid.

Another aspect of the present invention involves adding one or more antibiotic substance at one or more times during the processing period so that the resulting concentrated platelet composition contains either one or a variety of the antibiotics. The use of an antibiotic in concentrated platelet compositions that enhances the complex healing cascade is indeed novel. The invention disclosed herein involves adding such substances in a manner that does not detract from, substantially interfere with, or even destroy these different reactions, pH balances and potency. Another aspect of the present invention involves adding one or more vitamins known to promote wound healing, such as vitamin A and vitamin E.

The method of making the invention in gel form described herein includes mixing at least one of the described additives with the plasma-poor concentrated platelets, a sufficient time before the addition of calcified thrombin (or other preferably-calcified agonist) to allow the desired dispersion of such additive(s) in such composition before gelation prevents further dispersion.

DETAILED DESCRIPTION OF THE INVENTION

Before the present invention is described in detail, it is to be understood that the invention is not limited to the particular configurations, process steps and materials expressly disclosed herein; the invention includes those that are implicit or inherent in the disclosures set forth herein, and all legal equivalents of any element(s) or limitation(s) thereof As an example, the biological materials specified herein may originate from a patient to be treated, from a single third party, or from a plurality of third parties; moreover, said third parties may be of the same species as the patient, or of another species, so long as the wound treatment material derived from such biological materials is biocompatible with the patient. As another example, when the invention calls for a particular substance, it is sufficient to use any form of that substance having the characteristic(s) needed to satisfy the stated need; for instance, unless the context indicates otherwise, a need for growth factors may be satisfied by providing isolated growth factors or those that are included in platelets or other types of cells, and/or combinations thereof Similarly, the process deployed to obtain the growth factors may be any process that satisfactorily does so, regardless of whether it includes centrifugation.

It is also to be understood that the terminology used herein is not intended to be limiting, since the scope of the present invention will be limited only by the claims and equivalents thereof. Also, as used herein, the singular forms include the plurals, and vice versa, unless the context indicates otherwise.

For the sake of simplicity and to give the claims of this patent application the broadest interpretation and construction possible, the following definitions will apply:

(a) The phrase blood collecting or blood extraction (or similar phrase) includes techniques, materials and apparatus known in the field, such as (for example) inclusion of anticoagulation materials, the use of blood drawing and infusion apparatus.

(b) The phrase growth factor means any material(s) promoting growth of tissue.

(c) The term thrombin may include calcified thrombin, in particular, about 5,000 units of thrombin per ml of aqueous calcium chloride; it may include calcified bovine thrombin as well as autologous thrombin.

(d) The term viscosity means those characteristics of the specified material(s) determining the degree of gelation, such as (for example) the firmness or hardness of the material, or the degree to which the material resists flowing like a fluid.

(e) The term therapeutically effective amount means the amount or amounts of the constituent elements or combination thereof necessary to enhance wound healing such as, for example, the reduction in the volume or surface area of a wound, the increase in the amount of granulation tissue or other biological material facilitating collagen laydown, vascular in growth, fibroblast proliferation or overall healing; all of the versions of the invention described herein are assumed to have the therapeutically effective amount(s) of constituent substances, or combinations thereof Also for the sake of simplicity, the conjunctive "and" may also be taken to include the disjunctive "or," and vice versa, whenever necessary to give the claims of this patent application the broadest interpretation and construction possible. Likewise, when the plural form is used it may be taken to include the singular form and vice versa.

In most general terms, the invention includes a wound healant composition comprising activated growth factors and ascorbic acid. In the prevalent version of the invention, said growth factors are included within platelets. The body produces many substances generally known as growth factors, and the growth factors of the present invention are selected from the group consisting of platelet-derived growth factor (PDGF), platelet-derived angiogenesis factor (PDAF), vascular endotheial growth factor (VEGF), platelet-derived epidermal growth factor (PDEGF), platelet factor 4 (PF4), transformiing growth factor β (TGF-B), acidic fibroblast growth factor (FGF-A). basic fibroblast growth factor (FGF-B), transforming growth factor a (TGF-A), insulin-like growth factors 1 and 2 (IGF-1 and IGF-2), β thromboglobulin-related proteins (BTG), thrombospondin (TSP), fibronectin, von Wallinbrand's factor (vWF), fibropeptide A, fbrinogen, albumin, plasminogen activator inhibitor 1 (PAI-1), osteonectin, regulated upon activation normal T cell expressed and presumably secreted (RANTES), gro-α, vitronectin, fibrin D-dimer, factor V, antithrombin III, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL- 1), and combinations thereof. One ofthe important characteristics common to each substance, supporting the inclusion of each in this particular group, is that each such substance is known or believed to enhance cell or tissue growth. Moreover, said substances, or various combinations thereof, are known or believed to function together in an unexpected synergistic manner to promote wound healing.

The platelets are separated from the red blood cells and white blood cells of whole blood, primarily through differential centrifuigation. However, the overall composition of the invention disclosed herein may contain incidental amounts of white blood cells, due to the fact that the platelets are rarely totally isolated from the other blood components. It is believed that the present invention contains only minimal or trace amounts of white blood cells; it is believed that the white blood cell count ofthe present invention typically will be below about 3 times $10^7$ cells/ml. The present invention does not remove water to achieve concentration of cells. The invention biomaterials is almost exclusively from platelets. The range of the mean platelet volume of the platelets being sequestered is in the range of about 6.6 to 8.4 femtoliters, with an average of about 7.7 femtoliters; this may indicate that the platelets being sequestered are relatively larger or younger than the overall population of platelets.

Activation of growth factors may occur in a variety of manners, by a variety of substances known as activators or agonists. In the invention described herein, said activation results from the inclusion of an activator or agonist selected from the group consisting of thrombin, collagen, serotonin, adenosine diphosphate (ADP) and acetylcholine (ACH), and combinations thereof. In a particular version ofthe invention, said growth factors ar Included within concentrated platelets, and said activation results from the inclusion of thrombin. One of the important characteristics common to each substance, supporting the inclusion of each in this particular group, is that each such substance is known or believed to enhance cell or tissue growth. Moreover, said substances, or various combinations thereof, are known or believed to function together in an unexpected synergistic manner to promote wound healing.

The invention is not limited to autologous biological materials, such as where said concentrated platelets are obtained from the wounded's own biological material. The invention encompasses the use of biological materials obtained from one or more third parties, that need not be of the same species as the patient whose wound is being treated with the wound healant composition described herein unless bioincompatibility would result from the use of such third party biological materials.

In one general version ofthe invention, the wound healant composition includes concentrated platelets, thrombin and ascorbic acid. Ascorbic acid is known to have preservative properties, unless it is broken down such as occurs after exposure to sunlight or another source of ultraviolet (UV) light rays. However, most versions of the invention described herein are covered by bandages or otherwise shielded from UV rays almost immediately after application to the wound site.

Since the admixture of thrombin or other agonists will activate growth factors, the thrombin (or other agonists/activators) should usually be the last substance to be mixed immediately before it is desired that the gelatinous state be set up.

Another version of the invention includes the inclusion of at least one retinoid in the admixture, in addition to or in substitution of the ascorbic acid. Although the wound healant composition could include a combination of retinoids, one version of the invention merely includes vitamin A in addition to or in substitution of the ascorbic acid. Vitamin A has been known to counteract a side effect of some treatments using steroids, namely, the depressed reactivity of the body immune system to stimuli. Furthermore, vitamin A is known or believed to inhibit or decrease the bioactivity of manganese, magnesium and copper in the cellular and interstitial environment; said elements are known or believed to be active or instrumental in the laying down of keloids and scar tissue. (See, *Effects of Pantothenic Acid and Ascorbic Acid Supplementation on Human Skin Wound Healing Process* by Vaxman et al., Eur. Surg. Res. 1995, 28:4, 158–166.) The versions of the invention described herein containing vitamin A accordingly are believed to promote healing without as much scarring or keloid formation. In another version, said retinoid is vitamin E, known to facilitate healing. In any event, the vitamins disclosed herein (or combinations thereof) appear to enhance wound healing in an unexpectedly synergistic manner.

The utility and function of said vitamins are independent of any anti-oxidative properties. It should be recognized that none of said vitamins in this invention likely exhibits any anti-oxidative properties when applied topically and exposed to UV rays, as in Martin. UV rays rapidly break dowm such vitamins, or otherwise render them virtually impotent; moreover, any anti-oxidative properties are exhibited when the vitamin is absorbed internally, not via mere topical application.

Furthermore, the utility and function of said vitamins to the invention disclosed herein have other distinct differences from the utility and function of the vitamins to the Martin composition. For example, the ascorbic acid lowers the pH of the surrounding media, and thus makes it more difficult for saprophytic bacteria to grow in the wound bed.

Although the wound healant composition could include a combination of antibiotics, one version of the invention merely substitutes at least one antibiotic in addition to or in substitution of the ascorbic acid. Since many wound sites are either already infected with bacteria or are susceptible to such infection, it is desirable that a wound healant composition be capable of either killing bacteria or preventing the mobility or reproduction of bacteria. The invention described herein includes a wound healant composition comprising concentrated platelets, thrombin and at least one antibiotic. In particular, the invention includes a wound healant wherein said antibiotic is bacteriocidal to at least the Pseudomonas and Klebsella genera of bacteria, which are prevalent at wound sites and difficult to guard against. Alternatively, said antibiotic is selected from the group consisting of a neosporin, vancomycin and gentamycin, and combinations thereof. One of the important characteristics common to each substance, supporting the inclusion of each in this particular group, is that each such substance is known to kill said bacteria.

As indicated above, the invention may include a wound healant composition comprising concentrated platelets, thrombin, ascorbic acid, at least one retinoid and at least one antibiotic bacteriocidal to the Pseudomonas and Klebsella genera of bacteria.

Aside from the wound healant substance to be applied to wound sites, the invention further includes a method of malting a wound healant composition. One manner of making the plasma-poor concentrated platelets of the present invention is to collect about 450 ml of whole blood in anticoagulant (such as sodium citrate or any similar anticoagulant known in the field). That blood is then centrifuged at at least one speed in the range of between about 2,000 rpms and 3,000 rpms (preferably about 2,400 rpms) for a duration of between about 15 minutes and 25 minutes (preferably about 20 minutes) to separate out a band (or similar grouping) of: (a) plasma and most white blood cells; (b) platelets (and incidental white blood cells); and (c) red blood cells. The platelet portion may then be re-centrifuged to further separate out plasma (and incidental white blood cells); said re-centrifuging may be at at least one speed in the range of between about 4,000 rpms and 5,600 rpms (preferably about 4,800 rpms) for a duration of between about 5 minutes and 10 minutes (preferably about 7 ½ minutes).

The final yield is about 40 to 50 ml of plasma-poor concentrated platelets (in trace or incidental amounts of residual plasma and white blood cells). Both the plasma/leukocyte portion and the red blood cell portion may be reinfused back into the patient. The plasma-poor concentrated platelets may then be activated by a mixture of thrombin and (preferably) calcium. Preferably, a solution comprising 5,000 units of thrombin per ml of calcium chloride solution will result; since blood anticoagulants typically tie up blood calcium to prevent the clotting cascade from occurring, calcified thrombin is used to re-supply the plasma-poor concentrated platelets with more calcium to facilitite the clotting cascade at the wound site. Depending upon the relative concentrations of the ingredients, the resulting mixture may be either a liquid, or it may set up as a hard material or (preferably) as a gel having a viscosity dependant upon the relative amounts of thrombin and platelets; the relative concentrations of calcified thrombin to platelets determines how quickly the composition sets up, and how hard it will eventually be. Some mixtures will yield a composition that will set up in a gel in several seconds, whereas some mixtures will yield a composition that takes several minutes to set up in a gel.

Regardless of the amount of set up time, the present invention includes a preservative that allows the gel to retain its viscosity for a longer duration. For example, ascorbic acid is believed to preserve the longevity of the gel viscosity. Another method of making the wound healing composition includes the steps of mixing activated growth factors with ascorbic acid. Said activated growth factors may be obtained in a variety of ways, such as by the steps of sequestering concentrated platelets from blood and mixing thrombin with said platelets. Said ascorbic acid should be in sufficient amount to enhance the preservation of the gelatinous state of the final wound healing composition, and said thrombin should be in sufficient amount to facilitate formation of the coagulum (gel) having the desired level of viscosity while sufficiently activating growth factors present in the composition and the wound.

In one preferred version of the composition, about 1 ml of ascorbic acid is mixed with about 8 ml of concentrated platelets, then about 1 ml of calcified thrombin is mixed into that 9 ml admixture. However, other ratios of concentrated platelets:ascorbic acid:thrombin may be useful, depending upon the desired amount of healing agents, gelation time, gel viscosity and longevity.

Another method of making the composition allows the extraction of blood, sequestering of plasma-poor concentrated platelets, mixing of additives and return of unused blood components to the patient, all in about 20 to 30 minutes and by making only one puncture in the patient. Approximately 125 to 250 ml of blood is extracted from a patient, with the blood drawing apparatus optionally remaining in place connected to the patient (for later use in returning unused blood components to the patient). That blood is transferred to a Lathum bowl and, using a centrifige such as is manufactured by Haemonetics, Inc., centrifiged at about 4,800 rpms until a band (or similar grouping) of plasma formn at the upper perphery (about 5 to 15 minutes), and a band (or sirilar grouping) of red blood cells forms at the bottom of the bowl; the center is comprised of plasma-poor concentrated platelets. The plasma band is removed for return to the patient, and the remaining blood components are again centrifuged at that speed (and sufficient duration), further removing plasma and white blood cells from the plasma-poor concentrated platelets. The plasma-poor concentrated platelets are then removed for mixing with the other additives described herein (thrombin, ascorbic acid and/or retanoids).

The method of making a wound healant may further include, prior to or contemporaneous with mixing said thrombin, mixing at least one of the aforementioned retinoids in sufficient amount(s) to further enhance wound healing. In one version, 1 ml of aqueous vitamin A and vitamin E solution is added to 8 ml of concentrated platelets and 1 ml of ascorbic acid, before mixing in 1 ml of thrombin.

Alternatively, said method may include, prior to or contemporaneous with mixing said thrombin, mixing at least one of the aforementioned antibiotics in sufficient amount(s) to reduce infection by bacteria.

Besides a method of making a wound healant composition, the invention described herein may also include a method of treating a wound, comprising the steps of applying a sufficient amount of a composition of matter comprising growth factors and ascorbic acid to enhance healing of the wound.

Said method of treating a wound may include the use of any of the compositions described herein; it may also include the use of any composition made by any of the methods described herein.

Once applied to a wound, the composition may remain on the wound for as long as 5 days, and perhaps longer depending on the circumstances such as the location of the wound and other wound characteristics. Although the composition and method described herein are especially useful for the treatment of chronic wounds, they may also be useful in the treatment of acute wounds.

EXAMPLE 1

Case study: a 57 year old white male truck driver with a right heel diabetic ulcer of 11 month's duration. His treatment regimen has consisted of rest, off-loading and daily wound cleansing with soap and water followed by application of gauze dressing. Carrasyn gel was ordered for a brief period, without improvement. Upon referral to an outpatient physical therapy department for wound treatment, P's current therapy consists of weekly sharp debridement, wet saline gauze and total contact cast P has a history of hypertension, which is controlled at present time. He has a 15-year history of diabetes mellitus with neuropathy, which is controlled with oral hypoglycemic elements.

P began treatment with the invention disclosed herein. After his wound was sharply debrided, the gel coagulum was applied and the wound was covered with a wet saline dressing. A total contact cast was then applied and left intact for one week. At the conclusion of week 1 the cast was removed, the wound site cleansed and recovered with wet dressing; the limb was re-cast for week 2. After the conclusion of week 2, the same procedure was followed, except that the gel coagulum was again applied to the wound site before covering with wet dressing. After the conclusion of week 3 the same procedure as for week 2 was followed. This regimen continued for a total of 36 days. Table 1 below contains the data reflecting the reduction in wound site volume and surface area during weeks 1 through 4.

TABLE 1

| Week # | Volume (mm$^3$) | Area (mm$^2$) |
| --- | --- | --- |
| 0 | 3121 | 674 |
| 1 | 1561 | 562 |
| 2 | 279 | 301 |
| 3 | 26 | 282 |
| 4 | 15 | 159 | disclosed herein. Closure, on the average, took less than four weeks. The average patient wound was brought to 99% closure in 25 days.

| | Volume (mm$^3$) | | Area (mm$^2$) | |
| --- | --- | --- | --- | --- |
| Pt # | Start | End | Start | End |
| 1 | 3121 mm$^3$ | 15 mm$^3$ | 674 mm$^2$ | 159 mm$^2$ |
| 2 | 358 mm$^3$ | 0.0 mm$^3$ | 65 mm$^2$ | 4 mm$^2$ |
| 3 | 293 mm$^3$ | 3.0 mm$^3$ | 63 mm$^2$ | 3 mm$^2$ |
| 4 | 192 mm$^3$ | 18 mm$^3$ | 104 mm$^2$ | 39 mm$^2$ |
| 5 | 336 mm$^3$ | 0.0 mm$^3$ | 181 mm$^2$ | 0.0 mm$^2$ |

The five patients that entered into this study were referrals by their physicians. The patients were then screened using the exclusion, inclusion criteria. The patients selected for study had an ulcer of the lower extremity that had not healed after four to six months of treatment either with traditional wound care alone, or with traditional care plus Regranex[1].

[1] A single growth factor product of Ortho-Mcreal marketed by Johnson & Johnson.

All five of the study patients had a platelet count of 100,000 cells/mm$^3$ or greater, and had a hemoglobin>10 g and a HCT of 30% or greater. The patients were evaluated for infection in the wound, and for osteomyelitis. None of the patient studied showed signs of infection, or bone involvement.

Aggressive debridement to essentially change the chronic wound to an acute one was used. The ulcer and surrounding callus were completely excised down to normal uninvolved tissue. All subjects were treated as outpatients. All patients agreed to be totally non-weight-bearing. With the exception of one, patients were supplied with a half-shoe that transferred weight to the unaffected area of the foot. The one patient not fitted with the half-shoe was fitted with a full cast of the lower leg. Direct questioning of patients and family assessed the compliance issue. Only one patient proved to be non-compliant. Patient's blood sugar exceeded 400mg/dl and she became disoriented and walked on her foot at post treatment day 2. This resulted in a re-treatment of patient 4[2]. Table 2 shows the wound size and volume at the conmnencement and conclusion of treatment with the coagilum.

[2] Pt#4 NG was non-compliant through out this study, missing three clinic visits.

I claim:

1. A method of making a wound healant composition comprising activating a composition comprising a therapeutically effective amount of platelet concentrate and an effective gel viscosity preservation amount of ascorbic acid.

2. The method according to claim 1, wherein said activation occurs by admixing the composition with thrombin.

3. The method according to claim 2, said method further comprising, prior to mixing said thrombin, admixing at least one retinoid in sufficient amount(s) to further enhance wound healing.

4. The method according to claim 3, said method further comprising, prior to mixing said thrombin, admixing vitamin A in sufficient amount to reduce any non-responsiveness of the wounded's immune system to stimuli, and vitamin E in sufficient amount to further enhance wound healing.

5. The method according to claim 2, said method further comprising, prior to admixing said thrombin, mixing at least one antibiotic in sufficient amount(s) to reduce infection by bacteria.

6. The method according to claim 5, wherein said antibiotic is at least bacteriocidal to Pseudomonas and Klebsella bacteria.

7. The method according to claim 5, wherein said antibiotic is selected from the group consisting of neosporin, vancomycin and gentamycin, and combinations thereof.

8. The method according to claim 2, further comprising the steps of, prior to mixing thrombin, admixing, in therapeutically effective amount(s), at least one retinoid and at least one antibiotic bacteriocidal to at least Pseudomonas and Klebsella bacteria.

9. A method of making a wound healant composition comprising the steps of:
 (a) providing platelet concentrate;
 (b) admixing the platelet concentrate with an effective gel viscosity preservation amount of ascorbic acid to form a mixture; and
 (c) admixing a therapeutic effective amount of the mixture with an effective platelet activating amount of thrombin so as to form the wound healant composition.

10. A method for treating a wound in a patient comprising the steps of:

(a) providing platelet concentrate;

(b) admixing the platelet concentrate with an effective gel viscosity preservation amount of ascorbic acid to form a mixture;

(c) admixing a therapeutic effective amount of the mixture with an effective platelet activating amount of thrombin so as to form a wound healant composition; and (d) applying an effective therapeutic amount of the wound healant composition to the patient's wound.

11. The method according to claims 9 or 10, wherein said platelet concentrate is obtained by the extracting blood from a patient, centrifuging said blood until the appearance of an essentially separate band of plasma, an essentially separate band of red blood cells, and an essentially intermediate grouping comprised of concentrated platelets therebetwein; removing said plasma band; centrifuging said remaining blood components to obtain concentrated platelets; removing said concentrated platelets.

12. The method according to claims 9 or 10, wherein said platelet concentrate is autologous.

13. A method of treating a wound in a patient comprising the steps of applying to a wound a composition comprising a therapeutically effective amount of activated platelet concentrate and a gel viscosity preservation amount of ascorbic acid.

14. The method according to claim 13, wherein said activation results from the inclusion of an agonist.

15. The method according to claim 14, wherein said agonist is selected from the group consisting of thrombin, collagen, serotonin, ADP and acetylcholine (ACH), and combinations thereof.

16. The method according to claim 13, wherein said activation results from the inclusion of thrombin.

17. The method according to claim 13, wherein said platelet concentrate is autologous.

18. The method according to claim 13, wherein said composition further comprising at least one retinoid.

19. The method according to claim 18, wherein said retinoid is vitamin A.

20. The method according to claim 13, wherein said composition further comprises vitamin E.

21. The method according to claim 14, wherein said composition further comprises at least one antibiotic.

22. The method according to claim 21, wherein said antibiotic is bacteriocidal to at least Pseudomonas and Klebsella bacteria.

23. The method according to claim 21, wherein said antibiotic is selected from the group consisting of a neosporin, vancomycin and gentamycin, and combinations thereof.

24. The method according to claim 13, wherein said wound healant composition further comprises at least one retinoid and at least one antibiotic bacteriocidal to Pseudomoinas and Klebsella bacteria.

* * * * *

UNITED STATES PATENT AND TRADEMARK OFFICE
CERTIFICATE OF CORRECTION

PATENT NO. : 6,303,112 B1
DATED : October 16, 2001
INVENTOR(S) : Charles E. Worden It is certified that error appears in the above-identified patent and that said Letters Patent is hereby corrected as shown below:

<u>Title page,</u>
Item [73], Assignee, insert -- Cytomedix, Inc., Deerfield, IL --

Signed and Sealed this

Twentieth Day of May, 2003

JAMES E. ROGAN
*Director of the United States Patent and Trademark Office*